(12) United States Patent
Hansen (10) Patent No.: US 11,058,216 B2
(45) Date of Patent: Jul. 13, 2021

(54) CONTROL OF A HEIGHT ADJUSTABLE TABLE USING FINGERPRINTS

(71) Applicant: Kessebohmer Produktions GmbH & Co. KG, Teck (DE)

(72) Inventor: Melf Hansen, Gondelsheim (DE)

(73) Assignee: Kessebohmer Produktions GmbH & Co. KG, Weilheim/Teck (DE)

( * ) Notice: Subject to any disclaimer, the term of this patent is extended or adjusted under 35 U.S.C. 154(b) by 0 days.

(21) Appl. No.: 16/336,362

(22) PCT Filed: Sep. 26, 2016

(86) PCT No.: PCT/EP2016/072858
§ 371 (c)(1),
(2) Date: Mar. 25, 2019

(87) PCT Pub. No.: WO2018/054504
PCT Pub. Date: Mar. 29, 2018

(65) Prior Publication Data
US 2019/0223586 A1    Jul. 25, 2019

(51) Int. Cl.
*A47B 9/00*    (2006.01)
*G06K 9/00*    (2006.01)
(Continued)

(52) U.S. Cl.
CPC .............. *A47B 9/00* (2013.01); *A47B 21/02* (2013.01); *A47B 21/04* (2013.01); *A47B 33/00* (2013.01);
(Continued)

(58) Field of Classification Search
CPC ... A47B 9/00; A47B 21/02; A47B 2200/0035; A47B 2200/0062; A47C 3/20
(Continued)

(56) References Cited

U.S. PATENT DOCUMENTS 5,884,882 A * 3/1999 Nada ................. A47B 21/00
108/147
6,286,441 B1 * 9/2001 Burdi ................. A47B 9/00
108/147

(Continued)

FOREIGN PATENT DOCUMENTS

CN    1227738 A    9/1999
CN    1559074 A    12/2004
(Continued)

OTHER PUBLICATIONS

International Search Report and Written Opinion received for PCT Patent Application No. PCT/EP2016/072858, dated Apr. 11, 2017, 17 pages (8 pages of English Translation and 9 pages of Original Document).
(Continued)

*Primary Examiner* — Jose V Chen
(74) *Attorney, Agent, or Firm* — Wombie Bond Dickinson (US) LLP; John J. Penny, Jr.

(57) ABSTRACT

A height adjustable table is disclosed, comprising at least one electrically height adjustable table column and a control device, wherein the height adjustable table comprises an operating element with at least one fingerprint sensor. Furthermore, a method is disclosed by which the height adjustable table can be controlled using the fingerprint of a user.

19 Claims, 5 Drawing Sheets

(51) Int. Cl.
*A47B 21/02* (2006.01)
*A47B 21/04* (2006.01)
*A47B 33/00* (2006.01)
*A47C 3/20* (2006.01)
*A61B 5/1172* (2016.01)

(52) U.S. Cl.
CPC ............ *A47C 3/20* (2013.01); *G06K 9/00006* (2013.01); *G06K 9/00013* (2013.01); *G06K 9/00087* (2013.01); *A47B 2200/0035* (2013.01); *A47B 2200/0062* (2013.01); *A47B 2220/0077* (2013.01); *A61B 5/1172* (2013.01)

(58) Field of Classification Search
USPC ........ 108/50.01, 50.02, 147; 297/158.2, 161, 297/135, 174 R, 143
See application file for complete search history.

(56) References Cited

U.S. PATENT DOCUMENTS

| | | | |
|---|---|---|---|
| 6,296,408 B1 * | 10/2001 | Larkin | A47B 83/001 400/681 |
| 6,352,037 B1 * | 3/2002 | Doyle | A47B 9/00 108/147 |
| 6,522,773 B1 | 2/2003 | Houdeau | |
| 7,439,694 B2 * | 10/2008 | Atlas | A47B 9/04 108/146 |
| 7,805,784 B2 * | 10/2010 | Lemire | A61G 7/0514 5/611 |
| 8,947,215 B2 * | 2/2015 | Mandel | G06Q 10/109 108/147 |
| 8,967,057 B2 * | 3/2015 | Quiring | B66F 7/0666 108/145 |
| 9,167,894 B2 * | 10/2015 | DesRoches | F16L 3/01 |
| 9,345,318 B2 * | 5/2016 | Kollreider | A47B 9/04 |
| 9,433,288 B2 * | 9/2016 | Voigt | A47C 1/0242 |
| 9,907,396 B1 * | 3/2018 | Labrosse | A47B 21/02 |
| 9,921,726 B1 * | 3/2018 | Sculley | H04L 67/12 |
| 9,969,216 B2 * | 5/2018 | Sigal | B60B 33/0094 |
| 9,999,971 B2 * | 6/2018 | Charlton | B25H 1/16 |
| 10,258,150 B2 * | 4/2019 | Lin | A47B 17/02 |
| 10,376,158 B2 * | 8/2019 | Desroches | A61B 5/0205 |
| 10,398,233 B2 * | 9/2019 | Hoyt | A47C 1/03 |
| 10,455,932 B2 * | 10/2019 | Lin | A47B 9/00 |
| 10,470,563 B2 * | 11/2019 | Keller | A47B 21/06 |
| 2004/0262143 A1 | 12/2004 | Camillo | |
| 2009/0140982 A1 | 6/2009 | Chen et al. | |
| 2010/0198374 A1 * | 8/2010 | Carson | G06Q 10/00 700/90 |
| 2011/0101739 A1 * | 5/2011 | De Lissandri | A47C 7/72 297/135 |
| 2012/0126072 A1 * | 5/2012 | Pettersson | A47B 9/04 248/157 |
| 2014/0285959 A1 * | 9/2014 | Riley | A47B 83/02 361/679.08 |

FOREIGN PATENT DOCUMENTS

| | | |
|---|---|---|
| CN | 1949141 A | 4/2007 |
| CN | 101640140 A | 2/2010 |
| CN | 104537365 A | 4/2015 |
| CN | 105394936 A | 3/2016 |
| CN | 105644478 A | 6/2016 |
| CN | 106937794 A | 7/2017 |
| WO | 2005/017839 A2 | 2/2005 |
| WO | 2010/073243 A1 | 7/2010 |
| WO | 2014/113873 A1 | 7/2014 |

OTHER PUBLICATIONS

International Preliminary Report on Patentability received for PCT Patent Application No. PCT/EP2016/072858, dated Apr. 4, 2019, 13 pages (7 pages of English Translation and 6 pages of Original Document).

* cited by examiner

CONTROL OF A HEIGHT ADJUSTABLE TABLE USING FINGERPRINTS

RELATED APPLICATIONS

The present application claims priority under 35 U.S.C. § 365 to PCT/EP2016/072858 filed on Sep. 26, 2016, the disclosure of which is incorporated herein by reference.

From the prior art electrically height adjustable tables are known comprising an input device for operating a height adjustment function for a table top by telescope-like extension or retraction of the table legs. If a user wishes to adjust the height of the table top, he has to press or hold a button or switch on the input device provided for this purpose, or a button on a display of the input device. The table top then changes its height in the selected direction until it reaches either an end stop or the user releases the button or switch.

Usually, a button for raising the table is provided on the input device, which is marked with an arrow pointing upwards as well as a button for lowering the table top, which is marked with an arrow pointing downwards.

Furthermore, it is known to store a preferred sitting and/or standing height of the user in a control device of the height adjustable table and recall it by means of a memory function if required. For this purpose, the input device displays several buttons, whereas by pressing a button, the respective table height can be actuated. The input device of the table for example comprises a button with the label "M1 ", as well as a button with the label "M2". If a user has adjusted his preferred table height for sitting by using the buttons "upward/downward", he may e.g. store exactly this height in the control device and assign it to button "M1" (or record it). If the table height of the table is subsequently adjusted, the user can return to the stored preferred table height for sitting at any time by pressing and holding the button "M1 ". It is irrelevant, whether the current table height is below or above the stored value (M1). Therefore, by pressing and holding the exemplary button "M1" the table can either be moved upward or downward, depending on whether the current table height is below or above the stored table height.

Due to legal regulations, height adjustable tables may not be adjusted automatically in Europe today due to a lack of redundant control systems. For this reason, e.g. the above mentioned button "M1" has to be pressed and hold during the complete adjustment procedure, although the control device is able to recognize in which end position the table is to be adjusted, namely to the stored height.

Problems arise from the prior art in this respect, for example when any number of employees in an open-plan office do not use a fixed workstation (writing table), due to external project work, travel activities or home office etc. Therefore, a writing table is used under some circumstances every day by another employee. In order to be able to use the above mentioned memory function in this constellation as well, each writing table would have to comprise a respective button for each employee, on which the respective preferred table height is stored and can be retrieved. This is not feasible for a large number of employees.

In order to solve this problem, two app solutions for smartphone use are known from the prior art. The employee can download a respective app to his smartphone and log on with the control device of a selected writing table, in order to individually adjust the stored desired height. A disadvantage here is that the employee must first call up the app before using the table, if it is set too low for sitting down, and only then the table can be adjusted by using the app or, for example, a button on the writing table, before the employee can take a seat at the table which is then set correctly.

It is an object of the invention to provide a method, a device and a system by which a height adjustable table can be adjusted simple and convenient to a desired height which is stored individually for a user.

This object is solved by an embodiment according to the independent claims. Advantageous further developments are subject of the dependent claims.

By equipping the operating element of a height adjustable table with a fingerprint sensor, it is possible to identify a user during operation of for example a height adjustment function. Furthermore it is possible to subsequently retrieve a parameter for this user by means of a control device and to execute the function operated by the user personalized. For example, a predetermined preferred table height for this user can be adjusted.

If for example, in an open-plan office 20 writing tables are arranged for 20 employees, but no table is permanently assigned to an employee, according to the prior art no employee can use the possibly provided memory function of his current table in a reasonable manner. The user can adjust and store a preferred table height for sitting at his current table, as well as a preferred height of the table top for standing. If the employee works the next day at another of the 20 tables, he cannot longer use the set preferred heights of the table top. Due to the embodiment according to the invention it is possible to store different preferred table heights for different users in a control device of a writing table. If a user now takes a seat at any table and operates a height adjustable table with his finger, according to the invention the control device of the table recognizes by means of a fingerprint sensor, which user performs the operation, in order to retrieve for example the stored preferred table height and adjust it individually for this user.

By preferably providing a central server that can be accessed by any number of tables or control devices, a dataset of parameters for different users can be centrally managed and, if required, changed centrally. Thus, it is not necessary to manage or update the datasets saved in each control device of each writing table separately.

By preferably providing a vertically arranged flip switch for operation, intuitive operation of the functions "upward/downward" is possible. Furthermore, only one single fingerprint sensor has to be provided under this flip switch in order to be able to personally operate two different functions.

By preferably providing at least two detection areas, a separate fingerprint sensor has to be provided under each detection area, however, it is also possible to detect an operation of several detection surfaces at the same time, in contrast to a flip switch, which can only be tilted either up or down.

By preferably combining a flip switch or detection area with a fingerprint sensor, a user can operate a personalization as well as a function (e.g. an adjustment function) through one operation step.

Preferably, the flip switch or the detection area displays a transparent surface, under which the fingerprint sensor is located.

By preferably starting an adjusting movement of the height adjustable table even before the operating user has been identified, and/or even before the stored parameters for the identified user have been determined or retrieved, a particularly fast response behavior can be achieved when operating the table. The time delay that may occur under certain circumstances due to time span until the user has been identified and/or until the stored parameters have been determined or retrieved will not be recognized by the user, since the adjustments process starts immediately after the user input.

DETAILED DESCRIPTION OF THE INVENTION

Figure 1:
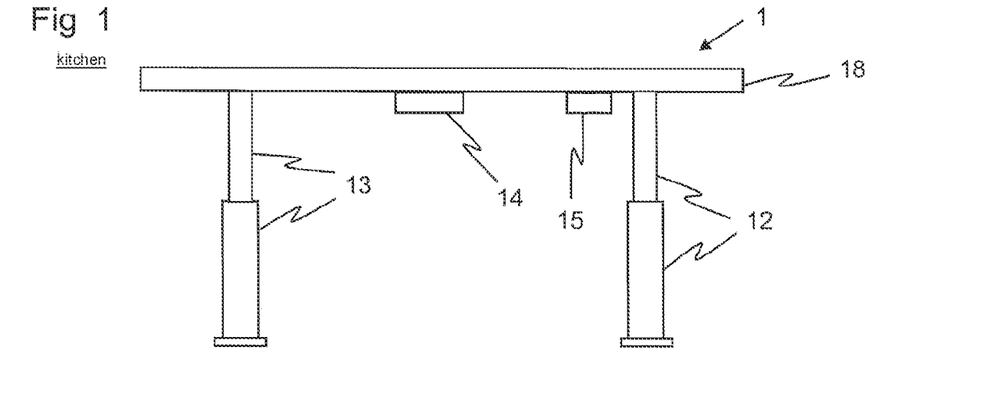
FIG. 1 shows an embodiment of a height adjustable table.

FIG. 1 shows an embodiment of a height adjustable table 1 with a table top 18 and two electrically height adjustable columns 12, 13. At the bottom side of the table top a control device 14 and an operating element 15 are arranged. Possible embodiments of the operating element 15 are discussed in relation to the following figures. In this embodiment the control device 14 comprises a memory device 141 which is adapted to store and provide parameters. The control device 14 is adapted to retrieve the parameters from the memory device 141 (internal communication) and to further processing them where appropriate. Furthermore, the control device 14 comprises a data interface for writing and reading parameters to and from the memory device 141 from outside (external communication). This data interface corresponds in the present embodiment to the type USB.

In a further embodiment not shown, the control device 14 comprises a data interface, which is adapted for (external) data communication via a wireless communication (WLAN and/or Bluetooth). In this embodiment, the memory device 141 is accessed externally via a wireless communication for writing and reading the parameters. The remaining configuration corresponds to the description of FIG. 1.

In a further embodiment not shown, the control device 14 does not have a memory device 141, but nevertheless comprises a data interface for (external) data communication. The data interface thereby either corresponds to a wired interface (e.g. USB) or a wireless communication interface (WLAN and/or Bluetooth). In this embodiment the control device 14 is adapted to retrieve the parameters via data interface (external) exactly when they are needed by the control device 14, for example from a server. In this embodiment the control device 14 may comprise a working memory, even if it does not comprise a memory device 141, to temporarily cache the parameters retrieved from the server (5). The remaining configuration corresponds to the description of FIG. 1.

In the embodiments described so far, the parameters comprise personalized information for any number of users. A parameter dataset contains at least one fingerprint of a user, as well as any number of additional information about exactly this user. This additional information includes e.g. a preferred table height for sitting at a table 1 (minimum table height), as well as a preferred table height for standing at a table 1 (maximum table height). Additional information about each user may also include, inter alia: a preferred orientation of an image output device arranged on the table (e.g. a monitor), for example the height of the monitor as well as the inclination of the screen of the monitor with respect to the surface of the table top 18; a preferred height of a seating equipment (e.g. a desk chair) arranged in front of the table 1; a preferred lighting configuration in the vicinity of the table 1; user credentials for unlocking a computer or workstation; a telephone number (extension) of a user; etc.

As an alternative to the wireless communication interface (WLAN and/or Bluetooth) mentioned above, any radio standard can be used in the height adjustable table 1 according to the invention.

Figure 2A:
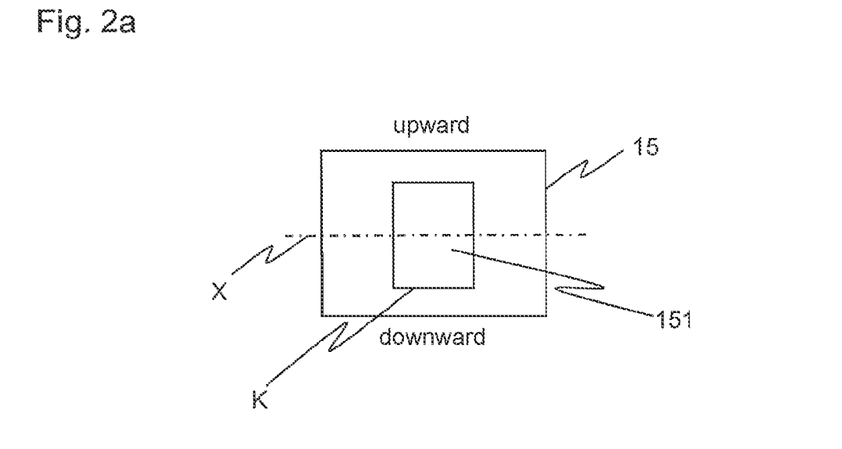
FIG. 2*a* shows an embodiment of an operating element.

FIG. 2*a* shows a possible embodiment of the operating element 15. In the embodiment shown, the operating element 15 comprises a flip switch K which can be tilted upward and downward about a horizontal axis. The flip switch K is adapted to be operated with a finger of the user. Furthermore, the flip switch K is adapted to return in its initial position (neutral position) if the flip switch is released, which is neither tilted upward nor downward. The flip switch K further comprises a fingerprint sensor 151, which is adapted to identify the fingerprint of the finger that touches the flip switch K.

The flip switch K is further adapted to transmit a signal to the control unit 14. The control unit 14 uses this signal to detect whether the flip switch K is touched by a finger, which fingerprint the finger has, and whether the flip switch K is in a neutral position, or whether it is tilted upward or downward.

Figure 2B:
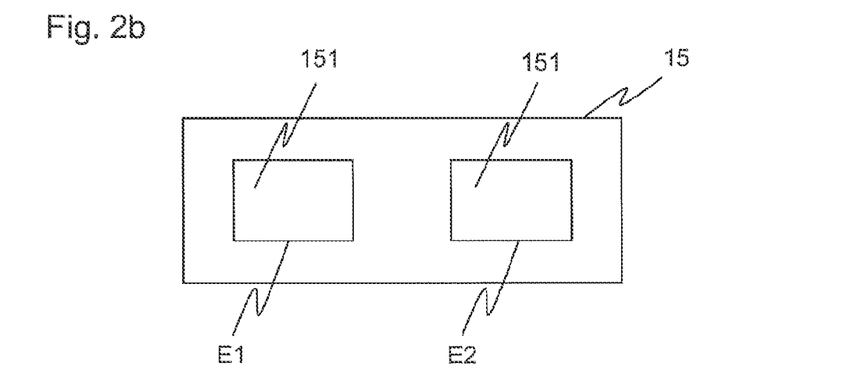
FIG. 2*b* shows a further embodiment of the operating element.

FIG. 2*b* shows a further possible embodiment of the operating element 15, wherein the operating element 15 comprises two detection areas (or buttons) E1, E2 instead of the flip switch K. Each of the detection areas E1, E2 comprises a fingerprint sensor 151. Furthermore, each of the detection areas E1, E2 is adapted to transmit a signal to the control device 14. The control device 14 uses this signal to detect, whether a detection area is touched by a finger and to recognize the fingerprint of the finger. The detection areas E1, E2 are arranged horizontally in this embodiment.

In a further embodiment not shown, the detection areas E1, E2 are adapted pressure-sensitive. Furthermore, in this case, the control unit 14 detects, whether a force is exerted on a touched detection area E1, E2, i.e. if the finger not only touches the detection area, but also pushes it. The remaining configuration corresponds to the description of FIG. 2*b*.

In a further embodiment not shown, the detection areas E1, E2 are arranged vertically on top of each other. The remaining configuration corresponds to the description of FIG. 2*b*, or alternatively to the above figure description to the pressure sensitive version.

Figure 3:
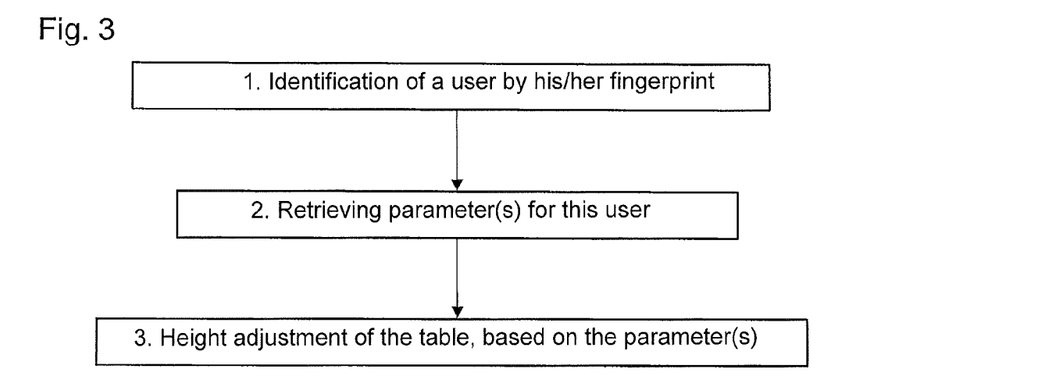
FIG. 3 shows is a method for individualized height adjustment of a table of an embodiment.

FIG. 3 shows a basic method for individualized height adjustment of a table, on which the following methods are based. In a first step, a user is identified by his or her fingerprint. This happens, for example, by capturing the fingerprint using one of the fingerprint sensors 151 described above (the flip switch K or the detection areas E1, E2). The captured fingerprint will then be compared, for example by a control device 14 as described above, to (stored or retrieved) datasets (internal communication) in order to read out the parameter(s) belonging to exactly this user. The parameter(s) is/are retrieved in a second step (see FIG. 3) for exactly this user to whom the captured fingerprint belongs.

The control unit 14 then decides which control action is to be executed based on the read parameter(s) and based on the concrete operation by the user's finger. For example, the control action to be carried out consists of height adjustment of a table 1 as described above, as shown in step 3 (see FIG. 3).

Figure 4:
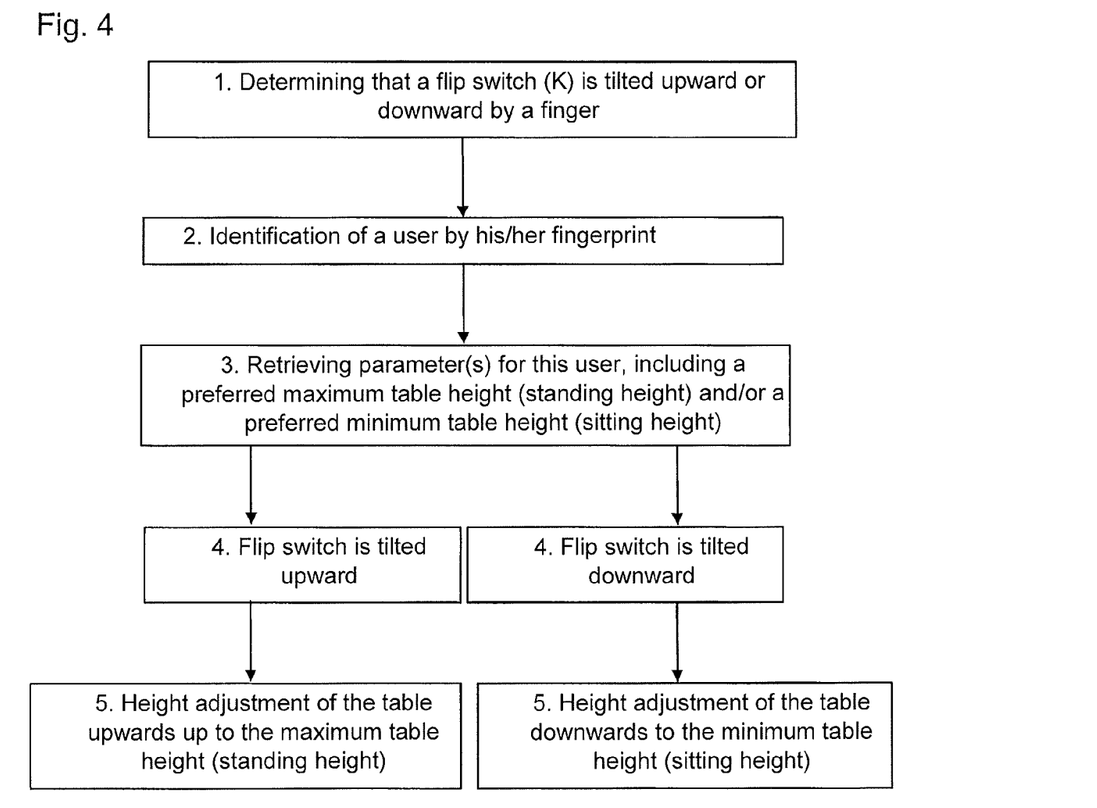
FIG. 4 shows another method of an embodiment of the invention.

FIG. 4 shows, in comparison to the method from FIG. 3, a more detailed method in order to explain a possible embodiment of the invention. A method is described, which is, for example, applicable using a table 1 with an operating element 15, in which a flip switch K with a fingerprint sensor 151 is provided, see FIG. 2*a*.

In a first step, the control device 14 determines, that the flip switch K is touched by a finger of a user. Furthermore, in this first step, it is determined that the flip switch K is tilted up or down by the finger. In a second step, the user is then identified by his fingerprint, following the same procedure as described above for FIG. 3.

Alternatively, the user can already be identified within the first step, even before a tilting of the flip switch K is recognized. With this alternative, it is only determined in the second step that the flip switch K is tilted upward or downward by the finger.

In a third step, parameters are then retrieved for the recognized user, for example by the control device 14, as explained with reference to FIG. 3. In the present embodiment, the parameters include a preferred table height for standing, as well as a preferred table height for sitting. In the present embodiment, it is also assumed that the initial table height is between this preferred table height for standing and this preferred table height for sitting.

In the following fourth step, the paths of the flow chart shown in FIG. 4 are separated. If the flip switch K is in an upturned state, the further course of the procedure corresponds to the left path. If the flip switch K is in a down tilted state, the further course of the procedure corresponds to the right path.

In the following fifth step, a height adjustment of the table 1 is started upward, in direction of the preferred table height for standing, if the course corresponds to the left path. Otherwise, if the course corresponds to the right path, a height adjustment of the table 1 is started downward, in direction of the preferred table height for sitting. The height adjustment is carried out until the respective preferred table height is reached. As a result, the height adjustment is stopped automatically. The height adjustment is also stopped, if the flip switch K is released by the user. This is due to the fact, that legal requirements for safety reasons currently prohibit the automatic adjustment of a height-adjustable table in many countries. From a technical point of view, this problem can be solved, as explained below.

In an embodiment not shown the height adjustment of the table 1 is not stopped, if the flip switch K is released by the user. In this embodiment a collision sensor is also provided, which recognizes a collision of the table top with 18 during the height adjustment. In the associated method, a collision of the table top 18 with objects is monitored during the adjustment process. If a collision is detected, the adjustment process is immediately aborted.

The above assumption that the initial table height lies between the preferred table height for standing and the preferred table height for sitting has been made in order to simplify the basic idea of the invention.

If the assumption does not apply, deviations in the procedure are provided. In this embodiment, the preferred height for standing is always adjusted, if the flip switch K is tilted upwards, even if the initial table height is above it. Here, the flip switch is tilted upwards although the height of the table 1 is then adjusted downwards. The state in which the original table height is below the table height for sitting is analogous to this.

In another embodiment not shown, the table 1 is always raised upward when the flip switch K is tilted upward for the first time (analogous to this, if the flip switch K is tilted downward for the first time, the height is adjusted downward).

Figure 5:
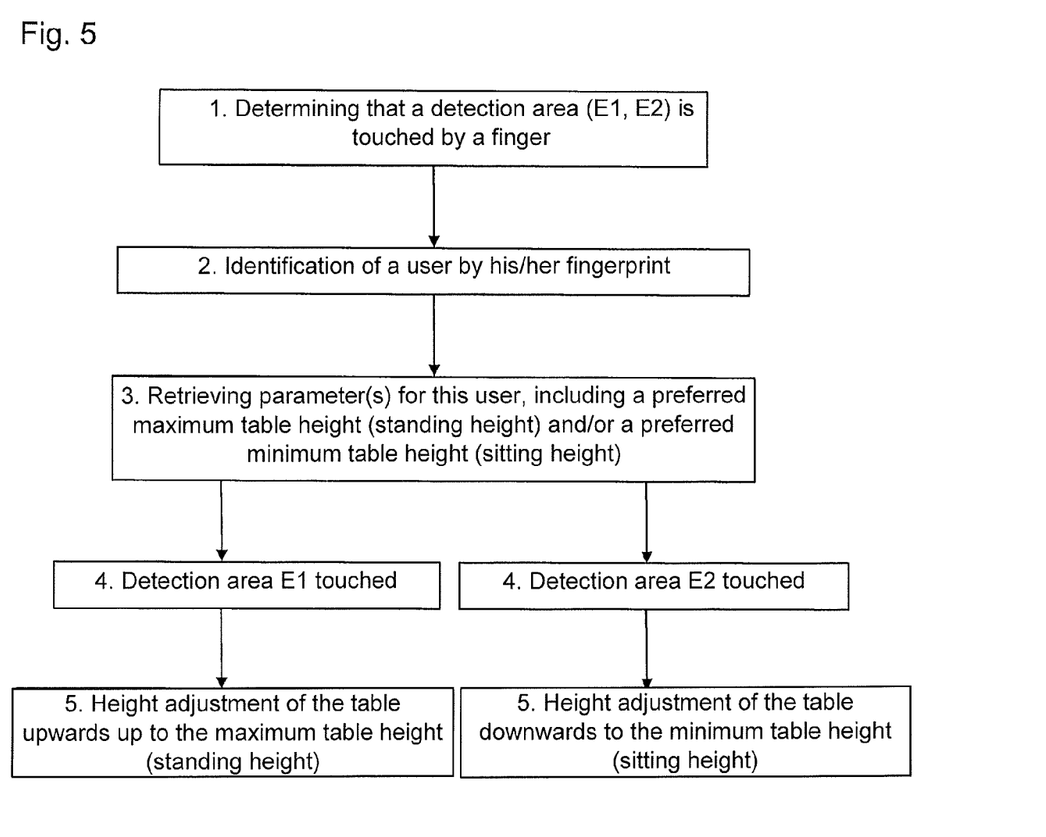
FIG. 5 shows another method of an embodiment of the invention.

Compared to FIG. 4, FIG. 5 shows a method that is applicable, for example, while using a table 1 with an operating element 15 with two detection areas E1, E2, each comprising a fingerprint sensor 151, see FIG. 2*b*.

The method shown in FIG. 5 works analogously to the method shown in FIG. 4, with the difference that it does not detect tilting of the flip switch K, but instead it detects the operation of at least one detection area E1, E2 by at least one finger of a user. Furthermore, in the embodiment shown in FIG. 5 the touching of the detection area E1 is assigned to the function "height adjustment to preferred table height for standing" and the detection area E2 is assigned to the function "height adjustment to the preferred table height for sitting".

Figure 6:
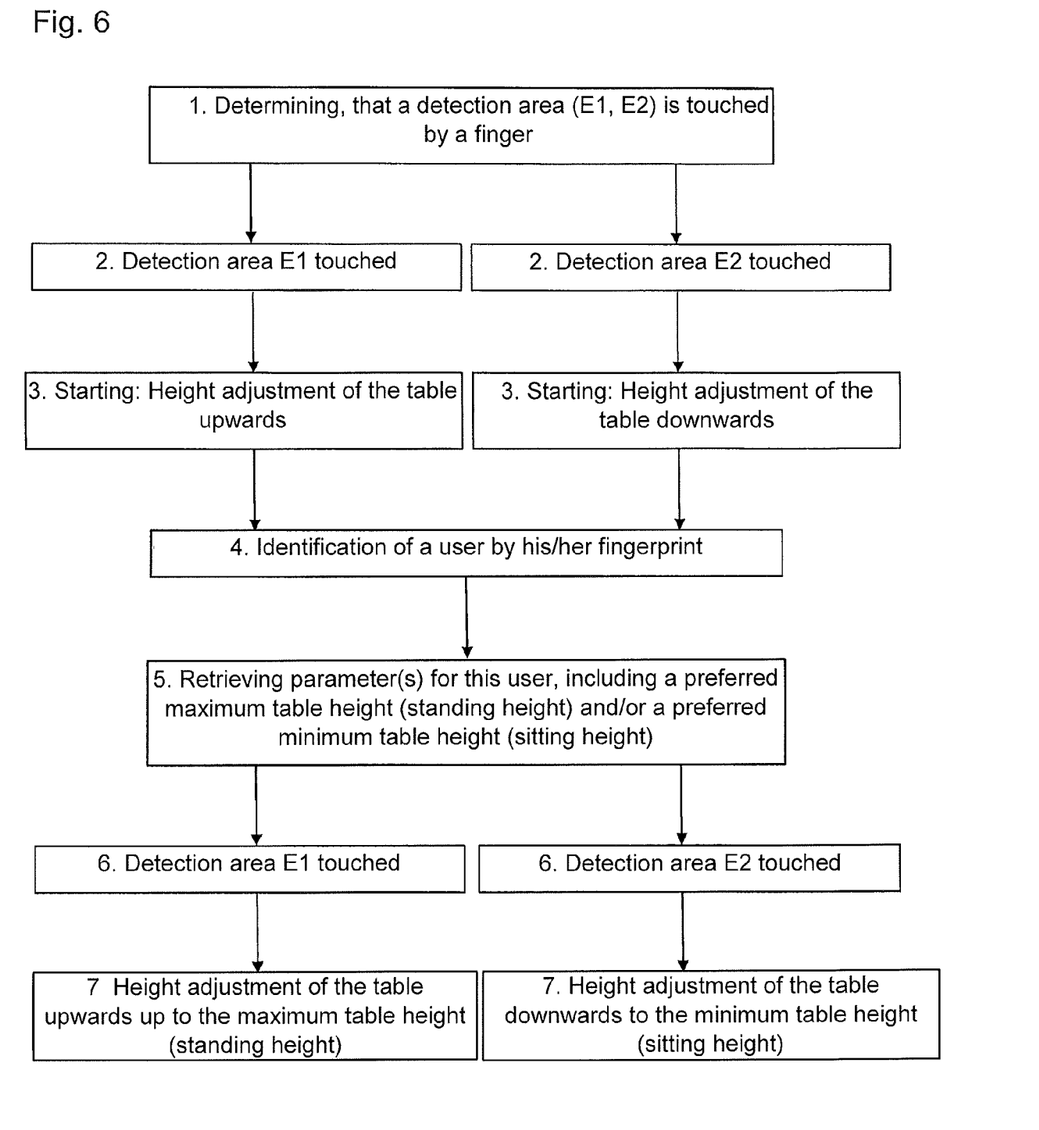
FIG. 6 shows another embodiment of the invention.

FIG. 6 shows an embodiment, where the identification of the user by his or her fingerprint is not performed immediately during steps 1 or 2, but only in a later step.

In this embodiment, it is determined in a first step that one of the detection areas is touched by a finger of a user. In the following next step, the second step, the paths of the procedure are already separated. In this embodiment, the actuation of the detection area E1 is assigned to the function "height adjustment to preferred table height for standing" and the actuation of the detection area E2 is assigned to the function "height adjustment to the preferred table height for sitting".

This assignment can be reversed in another embodiment, furthermore, other functions can be assigned to the detection areas E1, E2.

If, in this embodiment, it is determined that the detection area E1 is touched (step 1 or step 2), the height adjustment of the table upwards is already started during the third step. At this point, it has not yet been determined which user is currently operating the table and at which height the preferred positions for sitting/standing of this user lie. Only in the fourth step, the user is identified by his fingerprint during the height adjustment of the table. Thereupon, in the fifth step, the parameters for this user are retrieved, as for example the preferred table height for sitting and the preferred table height for standing. If the table is now adjusted upward, thus the detection area E1 is touched (see step 6, or already steps 2 and 3), the height adjustment is performed until the preferred table height for standing is reached. The operating principle for a height adjustment downward to a preferred table height for sitting by touching the detection area E2 works analogously.

In this embodiment, the height adjustment starts immediately after operating one of the detection areas E1, E2. Identification of the user and read out of the parameters belonging to the user is performed afterwards. Preferably, identifying the user as well as reading out the parameters is completed in less than one second after operating one of the detection areas E1, E2. This mode of operation can also be adapted to the version with a flip switch K. If furthermore an identification of the user is not possible in step 4, the height adjustment according to step 3 is performed until either an end position of the table top 18 is reached or until the detection areas E1, E2 are no longer touched.

As already discussed, in this embodiment the height adjustment starts immediately after operating one of the detection areas E1, E2, even before the user has been identified. If the user touches for example the detection area E1 in order to adjust the table to a preferred height for standing, a height adjustment of the table top 18 is started upward, in the direction of the preferred height for standing, even before the user has been identified. If, however, there is a time delay between step 3 and step 7, such that the height adjustment of the table top 18 has correctly been started upward during step 3, but the table top 18 has already reached too high a height before or during the operation of step 7, the height adjustment of the table top 18 is stopped according to an advantageous further development of the method. If thereupon the user further touches the detection area E1, the direction of movement of the table top 18 is reversed and a height adjustment of the table top 18 downward starts towards the preferred height for standing.

In a further embodiment not shown, anyone of the methods described above is adapted to adjust the table 1 generally upward by tilting the flip switch K upward or by actuating the detection area E1, regardless of the initial height of the table top 18, and generally downward by tilting the flip-switch K downward or by actuating the detection area E2, regardless of the initial height of table top 18. The parameters stored for the user "preferred table height for sitting" and "preferred table height for standing" are only breakpoints. If a table 1 is in a fully down position, and a user tilts the flip switch K upward or touches the detection area E1, the height of the table 1 or the table top 18 is adjusted upward. Depending on the adaption of the method (see above) the user has been identified and the corresponding parameters have been retrieved before or after starting the height adjustment. If now, when moving up from a lowest, maximum retracted position, a "preferred table height for sitting" is passed for the respective user, the table 1 stops automatically at this position (=breakpoint). The user can now release the flip switch K or the detection area E1. The table 1 remains in his current position. Alternatively, the user can keep the flip switch K tilted upward (or tilt it upward again), or further touch the detection area E1 (or touch it again). As a result, the table 1 starts moving again after a short break, for example after 2 seconds, and continues the height adjustment upwards, until the "preferred table height for standing" is reached. This height again represents a breakpoint. Analogously, the table 1 can thereupon be adjusted upwards, until a highest, maximum extended position. A height adjustment downward works analogous to this.

Figure 7A:
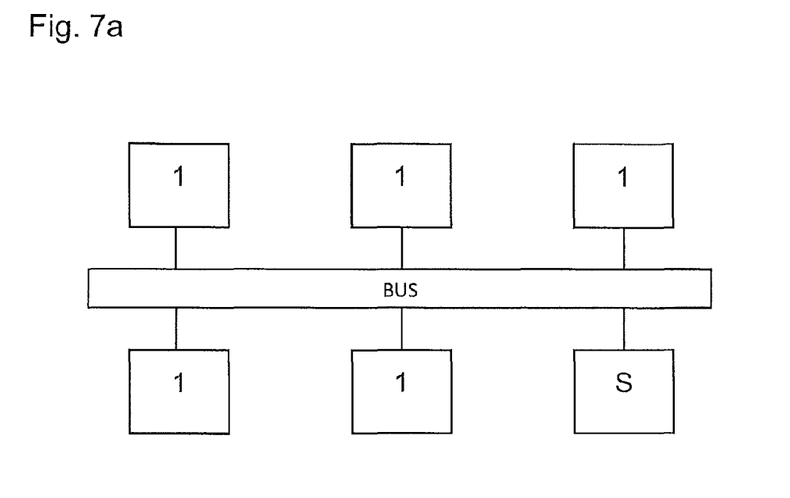
FIG. 7*a* is an embodiment for a system, wherein each writing table comprises a control device.

FIG. 7a shows an embodiment for a system, in which several height adjustable writing tables 1 are provided, wherein each writing table 1 comprises a control device 14. The writing table 1 are connected via a BUS-system with a server S, where each control device 14 is adapted to communicate via the BUS-system with the server S. For example, date sets can be retrieved by the control device 14 from the server S. Each of this data sets comprises at least one stored finger print of the respective user as well as further parameters for this user. These parameters comprise at least one of the following values: Preferred height of the table top for standing; preferred height of the table top for sitting; preferred height of a monitor for standing; preferred height of a monitor for sitting; preferred inclination of a monitor for standing; preferred inclination of a monitor for sitting; preferred height of a chair, preferred lightning configuration; credentials to log on to a computer or a workstation; telephone number or extension.

Figure 7B:
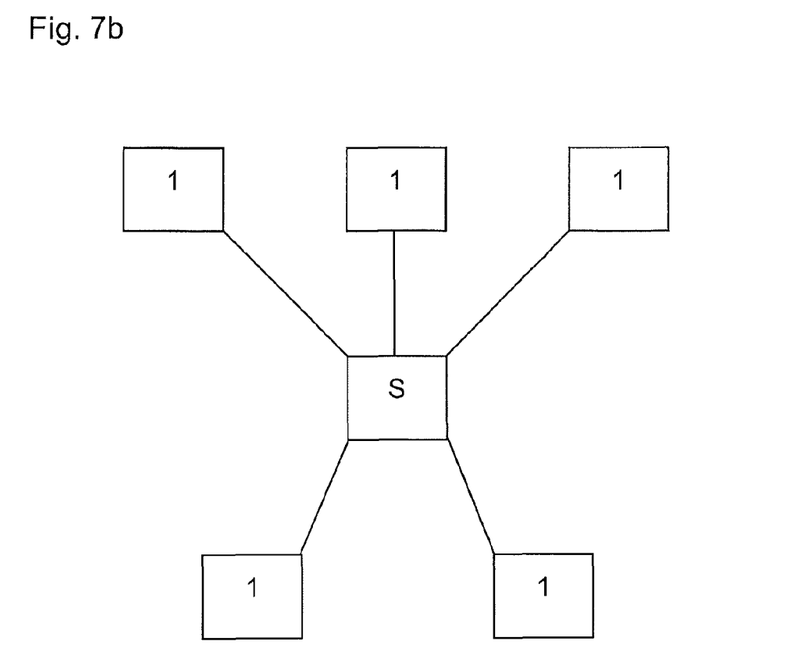
FIG. 7*b* is an alternative embodiment.

FIG. 7b shows an alternative configuration of the systems from FIG. 7a. In this configuration, the connection between the writing table 1 and the server S is not realized via a BUS-system, but via a star connection. The mode of operation is otherwise identical to the configuration from FIG. 7a.

In a further embodiment not shown, the table 1 comprises an interface to a mobile operating element alternatively or additionally to the operating element 15. This mobile operating element basically has the same functionality as the operating element 15, but the mobile operating element is assigned to a fixed user. Thus, the user can be identified by determining the identity of the mobile operating element. Furthermore, parameters assigned to the user can be stored on the mobile operating element, such as a preferred table height for standing. Furthermore, the mobile operation element could be designed as a mobile phone, tablet etc. with a corresponding app. Preferably, the interface is implemented between the table 1 and the mobile operating element or between the control element 14 and the mobile operating element via radio-frequency identification (RFID).

The invention claimed is:

1. A height adjustable table, comprising
at least one electrically height adjustable table column,
a control device, and
an operating element with at least one fingerprint sensor to identify a user, wherein the fingerprint sensor is provided in combination with a flip switch or as flip switch, which is set up to tilt around an axis upward or downward and which can be operated by a finger, wherein the operating element adjusts the height of the column when the fingerprint sensor and the flip switch are operated together in one step.

2. The height adjustable table according to claim 1, wherein the operating element is structurally integrated into the control device.

3. A kitchen comprising the height adjustable table according to claim 1.

4. A system comprising:
at least two height adjustable tables according to claim 1; and
a server, wherein the server is configured to manage data retrievable from the control devices of the height adjustable tables.

5. The system according to claim 1, wherein
the data consist of at least two sets of data, wherein each data set is assigned to a user, wherein each data set comprises at least one stored fingerprint of a respective user and further parameters for the user.

6. The system according to claim 5, wherein the parameters comprise at least one of the following values:
a preferred table top height for standing,
a preferred table top height for sitting,
a preferred height of a monitor for standing,
a preferred height of a monitor for sitting,
a preferred tilting of a monitor for standing,
a preferred tilting of a monitor for sitting,
a preferred height of a chair,
a preferred lighting configuration,
a login data for logging in to a computer or a workstation, and
a telephone number or extension.

7. The height adjustable table according to claim 1, wherein when the flip switch is tilted upward, the table is adjusted in the direction of a preferred maximum table height, and when the flip switch is tilted downward the table is adjusted in the direction of a preferred minimum table height.

8. A height adjustable table, comprising
- at least one electrically height adjustable table column;
- a control device; and
- an operating element comprising
    - at least two detection areas, each having a fingerprint sensor, wherein each detection area is provided to operate an adjustment function of the table when the fingerprint sensor and at least one detection area are operated together in one step.

9. The height adjustable table according to claim 8, wherein the operating element is structurally integrated into the control device.

10. A kitchen comprising the height adjustable table according to claim 8.

11. A system comprising:
- at least two height adjustable tables according to claim 8; and
- a server, wherein the server is configured to manage data retrievable from the control devices of the height adjustable tables.

12. A method for height adjustment of a table, comprising:
- identifying a user using a fingerprint from a fingerprint sensor;
- retrieving at least one parameter for the user;
- adjusting the height of the table, based on the parameter and the identity of the user;
- determining that a flip switch is switched upwards or downwards by a finger of the user;
- retrieving parameters for the identified user, comprising a preferred maximum table height and/or a preferred minimum table height; and
- adjusting the table in the direction of the preferred maximum table height, if the flip switch is tilted upward, or adjusting the table in the direction of the preferred minimum table height, if the flip switch is tilted downward, wherein the fingerprint sensor is part of the flip switch and the adjusting is performed during the identifying in one step.

13. The method according to claim 12, wherein the adjustment of the table based on a tilting direction of the flip switch is started before the user has been identified or before the parameters for the identified user have been retrieved.

14. The method according to claim 13, wherein adjustment of the table is started immediately after tilting the flip switch or immediately after touching the detection area.

15. The method according to claim 12, wherein using the identified user and based on parameters retrieved from the identified user and a current status, further comprising at least one of the following:
- height adjustment of a table top upward,
- height adjustment of a table top downward,
- height adjustment of a monitor upward,
- height adjustment of a monitor downward,
- tilting of a monitor forward,
- tilting of a monitor backward,
- height adjustment of a chair upward,
- height adjustment of a chair downward,
- light on,
- light off,
- login and/or share a computer or workstation
- locking of a computer or workstation, and
- switching a telephone to the extension of the determined user.

16. The height adjustable table according to claim 12, wherein adjusting the height of the table is stopped if the flip switch is released.

17. A method for height adjustment of a table, comprising:
- identifying a user using a fingerprint from a fingerprint sensor;
- retrieving at least one parameter for the user;
- determining that a detection area is touched by a finger, and determining using the fingerprint sensor, which detection area it is; and
- adjusting the table based on an adjustment function, which is associated with the touched detection area, the at least one parameter retrieved and the identity of the user, wherein the adjusting is performed during the identifying in one step.

18. The method according to claim 17, wherein the adjustment of the table based on an identity of the touched detection area is started before the user has been identified.

19. A method for height adjustment of a table, comprising:
- identifying a finger of a user using a fingerprint by a fingerprint sensor,
- retrieving a function for the identified finger,
    - executing the function, and
    - using the identified finger of a user and based on a current status, further comprising performing at least one of the following during the identifying in one step:
- height adjustment of a table top upward,
- height adjustment of a table top downward,
- height adjustment of a monitor upward,
- height adjustment of a monitor downward,
- tilting of a monitor forward,
- tilting of a monitor backward,
- height adjustment of a chair upward,
- height adjustment of a chair downward,
- light on,
- light off,
- login and/or share a computer or workstation
- locking of a computer or workstation, and
- switching a telephone to the extension of the determined user.

* * * * *

UNITED STATES PATENT AND TRADEMARK OFFICE
CERTIFICATE OF CORRECTION

| | | |
|---|---|---|
| PATENT NO. | : 11,058,216 B2 | Page 1 of 1 |
| APPLICATION NO. | : 16/336362 | |
| DATED | : July 13, 2021 | |
| INVENTOR(S) | : Melf Hansen | |

It is certified that error appears in the above-identified patent and that said Letters Patent is hereby corrected as shown below:

On the Title Page

Item (73) Assignee "Kessebohmer Produktions GmbH & Co. KG" should be changed to
-- Kesseböhmer Produktions GmbH & Co. KG --

Signed and Sealed this
First Day of August, 2023

Katherine Kelly Vidal
*Director of the United States Patent and Trademark Office*